United States Patent
Hendriks et al.

(10) Patent No.: US 10,383,584 B2
(45) Date of Patent: Aug. 20, 2019

(54) PHOTONIC NEEDLE SYSTEM WITH MEASUREMENT INTEGRATION TIMES DEPENDING ON NEEDLE DISPLACEMENT SPEED

(71) Applicant: KONINKLIJKE PHILIPS N.V., Eindhoven (NL)

(72) Inventors: Bernardus Hendrikus Wilhelmus Hendriks, Eindhoven (NL); Christian Reich, Eindhoven (NL); Rami Nachabe, Eindhoven (NL); Jeroen Jan Lambertus Horikx, Weert (NL); Arnoldus Theodorus Martinus Hendricus Van Keersop, Eersel (NL); Robert Johannes Frederik Homan, Batenburg (NL); Nicolaas Jan Noordhoek, Eindhoven (NL); Manfred Mueller, Eindhoven (NL); Jasper Klewer, Utrecht (NL); Marjolein Van Der Voort, Valkenswaard (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 786 days.

(21) Appl. No.: 14/383,716

(22) PCT Filed: Mar. 11, 2013

(86) PCT No.: PCT/IB2013/051900
§ 371 (c)(1),
(2) Date: Sep. 8, 2014

(87) PCT Pub. No.: WO2013/140293
PCT Pub. Date: Sep. 26, 2013

(65) Prior Publication Data
US 2015/0080711 A1 Mar. 19, 2015

Related U.S. Application Data

(60) Provisional application No. 61/614,558, filed on Mar. 23, 2012.

(51) Int. Cl.
*A61B 5/00* (2006.01)
*A61B 6/12* (2006.01)
(Continued)

(52) U.S. Cl.
CPC .............. *A61B 6/12* (2013.01); *A61B 5/0035* (2013.01); *A61B 5/0071* (2013.01);
(Continued)

(58) Field of Classification Search
CPC ......... A61B 34/20; A61B 6/12; A61B 6/5217; A61B 5/0035; A61B 5/7425; A61B 5/065;
(Continued)

(56) References Cited

U.S. PATENT DOCUMENTS 5,676,673 A * 10/1997 Ferre .................. A61B 34/20
606/1
6,432,065 B1 8/2002 Burdorff et al.
(Continued)

FOREIGN PATENT DOCUMENTS

GB 2467340 A 1/2009
WO 2007109540 A2 9/2007
(Continued)

OTHER PUBLICATIONS

Racadio, J.M. et al. (2007) "Live 3D Guidance in the Interventional radiology Suite" Am. J. Roentgenol. 189(6): W357-364.
(Continued)

*Primary Examiner* — Peter Luong (57) ABSTRACT

The present invention relates to a system (10) for guiding an instrument (12, 100, 100A, 100B, 112) in a body (14). The
(Continued)

system (10) records an image where the instrument (12, 100, 100A, 100B, 112) is identifiable and the instrument (12, 100, 100A, 100B, 112) records signals indicative of the type of tissue at the instrument (12, 100, 100A, 100B, 112). The system (10) determines the tissue type based on a signal from the instrument (12, 100, 100A, 100B, 112). The system (10) displays an image being a combined image of the body (14) and instrument (12, 100, 100A, 100B, 112) and an indication of tissue type at a position where the tissue type was determined. The present invention further relates to a method of displaying an image comprising tissue-type and instrument position in a body. The present invention further relates to an instrument and a software implemented method for being executed on a digital processor.

14 Claims, 3 Drawing Sheets

(51) Int. Cl.
| | | |
|---|---|---|
| | *A61B 5/06* | (2006.01) |
| | *A61B 6/00* | (2006.01) |
| | *A61B 34/20* | (2016.01) |
| | *A61B 90/30* | (2016.01) |
| | *A61B 90/00* | (2016.01) |

(52) U.S. Cl.
CPC .......... *A61B 5/0075* (2013.01); *A61B 5/0084* (2013.01); *A61B 5/065* (2013.01); *A61B 5/066* (2013.01); *A61B 5/6848* (2013.01); *A61B 5/7425* (2013.01); *A61B 6/5217* (2013.01); *A61B 34/20* (2016.02); *A61B 5/6852* (2013.01); *A61B 90/30* (2016.02); *A61B 90/361* (2016.02); *A61B 2034/2048* (2016.02); *A61B 2034/2051* (2016.02); *A61B 2034/2061* (2016.02); *A61B 2090/376* (2016.02)

(58) Field of Classification Search
CPC ..... A61B 5/066; A61B 5/6848; A61B 5/0071; A61B 5/0075; A61B 5/0084; A61B 5/6852; A61B 90/30; A61B 90/361; A61B 2090/376; A61B 2034/2051; A61B 2034/2061; A61B 2034/2048
See application file for complete search history.

(56) References Cited

U.S. PATENT DOCUMENTS

| | | |
|---|---|---|
| 9,179,985 B2 | 11/2015 | Hendriks et al. |
| 2002/0013525 A1 | 1/2002 | Scott |
| 2005/0021019 A1 | 1/2005 | Hashimshony et al. |
| 2009/0036794 A1 | 2/2009 | Stubhaug et al. |
| 2010/0274120 A1 | 10/2010 | Heuscher |
| 2010/0280364 A1 | 11/2010 | Lu et al. |
| 2010/0331782 A1 | 12/2010 | Hendriks et al. |
| 2011/0313299 A1 | 12/2011 | Brennan |
| 2014/0207008 A1* | 7/2014 | Davies .................. A61B 5/742 |
| | | 600/486 |
| 2015/0080711 A1 | 3/2015 | Hendriks et al. |

FOREIGN PATENT DOCUMENTS

| | | |
|---|---|---|
| WO | 2008068685 A1 | 6/2008 |
| WO | 2010143119 A2 | 12/2010 |

OTHER PUBLICATIONS

Nachabe, R. et al. "Estimation of biological chromophores using diffuse optical spectroscopy: benefit of extending the UV-VIS wavelength range to include 1000 to 1600 nm", Biomedical Optics Express 18 (2010) p. 1432.

Nachabe, R. et al. "Estimation of lipid and water concentrations in scattering media with diffuse optical spectroscopy from 900? to? 1600? nm", Journal of Biomedical Optics, vol. 15, No. 1, Jan. 1, 2010, p. 037015.

\* cited by examiner

PHOTONIC NEEDLE SYSTEM WITH MEASUREMENT INTEGRATION TIMES DEPENDING ON NEEDLE DISPLACEMENT SPEED

CROSS-REFERENCE TO PRIOR APPLICATIONS

This application is the U.S. National Phase application under 35 U.S.C. § 371 of International Application Serial No. PCT/IB2013/051900, filed on Mar. 11, 2013, which claims the benefit of U.S. Application Ser. No. 61/614,558, filed on Mar. 23, 2012. These applications are hereby incorporated by reference herein.

FIELD OF THE INVENTION

The present invention relates to a system for guiding an instrument in a body.

BACKGROUND OF THE INVENTION

When performing procedures involving introducing an instrument into a body it is advantageous for the person performing the procedure to be given a visual feedback regarding the position of the instrument. Further the person performing the procedure could benefit from information as to which type of tissue is present at the instrument.

Needles are one of many devices or instruments which are placed in specific locations within a body based on pre-procedural images. The images are obtained with various modalities (imaging technologies) such as magnetic resonance imaging, computed tomography or image reconstruction such as XperCT™. One goal of placement is to minimize damage to surrounding tissues by carefully selecting the path of the needle during placement.

With X-ray instrument guidance it is possible to allow for almost real-time monitoring of instrument guidance under for instance fluoroscopy. An optical needle is one example of a device configured to provide tissue feedback as guidance and information. The optical needle transmits an optical signal to the tissue and receives. By combining these two techniques both the instrument tip location with respect to the body as well as the display of tissue information at that location is possible.

To obtain tissue information using an optical signal optical spectra has to be acquired and processed to create the tissue information. Furthermore this information must be sent to the X-ray console, or other type of imaging device, linked to the instrument position in the image, and finally displayed. All these steps require an amount of time and may cause that the displayed data is no longer up to date with the actual location. Especially when the instrument is advanced relatively fast, the tissue information may be lagging behind.

The inventor of the present invention has appreciated that an improved system and method is of benefit, and has in consequence devised the present invention.

SUMMARY OF THE INVENTION

It would be advantageous to achieve an improved image feedback to the user. It would also be desirable to enable display of combined tissue information and instrument position during movement. In general, the invention preferably seeks to mitigate, alleviate or eliminate one or more of the above mentioned disadvantages singly or in any combination. In particular, it may be seen as an object of the present invention to provide a method that solves the above mentioned problems, or other problems, of the prior art.

To better address one or more of these concerns, in a first aspect of the invention a guidance system for guiding an instrument in a body is presented that comprises a medical imaging device configured for forming an image of the interior of the body, a tissue-type determination device configured to receive a tissue signal from an instrument, the tissue-type determination device configured to determine a set of parameters indicative of tissue type based on the tissue signal from the instrument, the tissue-type determination device being operable in two modes, a first mode where tissue-type determination is performed using a first accuracy and a second mode where tissue-type determination is performed using a second accuracy being higher than the first accuracy, the guidance system being configured for determining position of the instrument and storing a sequence of positions, the guidance system being configured for establishing a display image combining the image of the interior of the body and the set of parameters indicative of tissue type displayed at the recorded positions of the instrument, and a display device configured for displaying the display image. The system according to the first aspect provides a user with a visual feedback of instrument position and tissue information in one image. As tissue-type determination is cumbersome there is normally a risk that tissue-type information is displayed at a position at a large distance from the present position.

The instrument may in the present context be an interventional device. The instrument or interventional device may comprise a first guide for guiding photons from the light source to an exit position on a distal end of the interventional device, the photons being emittable from the exit position, and a second guide for guiding photons from an entry position on the distal end of the interventional device and to the optical detector.

It is understood that in one particular embodiment, the first guide and the second guide may be one guide, such as the first guide is identical to the second guide. In another particular embodiment, the first guide and the second guide are two separate guides.

An interventional device is generally known in the art, and may include any one of an endoscope, a catheter, a biopsy needle. Integrating optical fibers in the interventional device allows inspection of the optical characteristics of the tissue sample and may allow discrimination of pathology tissue from normal tissue. In a particular embodiment, there is provided an interventional device being suited both for Diffuse Reflectance Spectroscopy (DRS) and/or fluorescence spectroscopy. It is noted that the constraint that the interventional device should be applicable for fluorescence spectroscopy puts some additional constraints on the interventional device. For instance the fibres used for fluorescence spectroscopy must not produce too much autofluorescence themselves and the separation between fibre ends for the fibres respectively connected to source and detector may be shorter compared to the same distance for DRS.

In another embodiment according to the invention, the exit position and the entry position are spatially separated and spatially oriented so that the entry position is not intersected by ballistic photons emitted from the exit position, when the distal end of the interventional device is placed adjacent the associated sample. It is understood that the entry position is not intersected by ballistic photons emitted from the exit position, at least from a practical point of view. For all practical purposes, the number of ballistic photons hitting the entry position is non-zero but negligible.

The system provides at least two levels of calculation accuracies so that in periods where the instrument is moved a great distance the accuracy is reduced thereby lowering the calculation time. The accuracy level may be defined in different ways. One is to determine the level of noise in the signal, where a low level of accuracy allows a high level of noise, and a high level of accuracy allows only a lower level of noise. In the high accuracy mode a relative threshold of 10% to 80% of the noise level in the low accuracy mode could be defined, such as relative threshold of 20% to 50%, such as 30% to 40%, such as 10% to 20%, such as 20% to 30%, such as 30% to 40%, such as 40% to 50%, such as 50% to 60%, such as 60% to 70%, such as 70% to 80%, or any other suitable value. In other embodiments the level of accuracy could be defined by a number of iterations that are used for determining a parameter from a spectrum of an optical signal, as will be discussed in the relevant embodiments below.

During any procedure accurate knowledge about the location of the needle tip is important, but proper guidance relative to the image may not be available. For instance, in the case of a CT guided biopsy, the number of images acquired is limited due to concerns about radiation exposure to the patient. If, due to the lack of precise information, incorrect tissues are targeted, there is a risk of an inaccurate diagnosis or a need for repeated procedures, which involves additional risk to the patient and increased costs.

One method of tracking the position of the needle tip relative to pre-procedural image is to place a marker(s) on the portion of the needle external to the patient and to track the marker in real time by means of a variety of sensors; given an estimation of the needle geometry the computed needle tip position can then be mapped in real time to the pre-procedural image. For instance, optical tracking of the needle can be performed with visual markers using two or more imaging cameras. Alternatively, Electro-Magnetic (EM) navigation can be performed by means of a small EM coil marker placed on the needle and tracked by a set of sensors external to the needle.

While the location and orientation of the tip is important, the real-time information relating to the tissue in front of the instrument is also important to the person operating the instrument.

Advantageously the guidance system may further comprise an instrument speed analyzer for determining present speed of the instrument, if the present speed of the instrument is above a speed threshold the tissue-type determination device being operated in the first mode, if the present speed of the instrument is below a speed threshold the tissue-type determination device being operated in the second mode. By providing an automated detection of movement speed the user is alleviated from the burden of having to select an accuracy level. This could e.g. be useful when the instrument is being operated by a person that does not wish to interact with the system during the procedure.

Advantageously the speed threshold is in the range 0.5 mm/second to 100 mm/second, such as 1 mm/second to 20 mm/second, such as 1.5 mm/second to 5 mm/second, such as 2 mm/second to 3 mm/second, such as 0.5 mm/second to 1 mm/second, such as 1 mm/second to 1.5 mm/second, such as 1.5 mm/second to 2 mm/second, such as 2 mm/second to 3 mm/second, such as 3 mm/second to 5 mm/second, such as 5 mm/second to 10 mm/second, such as 10 mm/second to 15 mm/second, such as 15 mm/second to 25 mm/second, such as 25 mm/second to 50 mm/second, such as around 1 mm/second. The threshold may be manually selected by an operator prior to, or during, a procedure.

Advantageously the guidance system may further comprise an input device for supplying a tissue-type determination mode signal to the tissue-type determination device instructing the tissue-type determination device to operate in the first mode or the second mode. In situations where the user wishes to have complete control of the operation of the system it could be advantageous to provide an input device so that the user can manually set the accuracy level at any time.

As mentioned the medical imaging device comprises an x-ray device. This is a common medical imaging device which provides an image that is readily accepted and persons operating such instruments are used to interpret such images.

Advantageously the tissue-type determination device is an optical console obtains an optical spectrum, and processes the optical spectrum to determine the set of parameters indicative of tissue type. Using an optical signal to determine tissue parameters is a non-invasive method of investigating tissue. Using the optical signal further damage to the tissue is avoided.

The guidance system may further comprise a mode indicator for communicating to a user if the tissue-type determination device operates in the first mode or the second mode. By providing information to the user regarding which current mode is applied the user knowledge base is increased and he or she is made aware that information displayed have a given quality or certainty.

In an embodiment the guidance system may comprises a processor arranged for receiving signals relating to the set of parameters indicative of tissue type and the sequence of positions of the instrument, the processor being arranged for establishing the display image. The processor may be a digital processor adapted for executing a software implementation of a method for performing the calculations and determinations of different parts of the process as described herein.

The tissue-type determination device may be an optical console and the guidance system may be arranged so as to obtain a diffuse reflectance spectrum and/or fluorescence spectroscopy spectrum and/or Raman spectrum from the optical console. Light is to be broadly construed as electro-magnetic radiation comprising wavelength intervals including visible, ultraviolet (UV), near infrared (NIR), infrared (IR), X-ray. The term optical is to be understood as relating to light.

An optical spectrum is understood to be information related to a plurality of wavelengths of light, such as an intensity parameter, an absorption parameter, a scattering parameter or a transmission parameter given for a plurality of wavelengths of light. A continuous spectrum represents spectral information, but it is further understood, that information related to light at discrete wavelengths may represents an optical spectrum.

A spectrometer is understood as is common in the art. It is understood, that the spectrometer comprises means for selecting wavelengths, such as transmission filters or gratings. Alternatively, wavelength specific light sources, such as light emitting diodes or LASERs, may be used or wavelength specific optical detectors may be used. A spectral filtration may occur at different places in the system, for instance it may occur between the second light source and an interventional device, it may occur in the interventional device, or it may occur between the interventional device and the optical detector.

In an embodiment the determination of to the set of parameters indicative of tissue type comprises fitting the data to a mathematical model, and performing multivariate statistical analysis, such as PCA or partial least squares discriminant analysis. Multivariate analysis is commonly known in the art and understood to include Principal Components Analysis (PCA) and least squares discriminant analysis.

A second aspect of the present invention relates to a method of displaying an image comprising tissue-type and instrument position in a body, the method comprising the steps of recording a sequence of images of the interior of the body each at time Ti, determining an instrument position in each image of the interior of the body, determining at a tissue parameter at a tip of the instrument at time Tt and an estimated instrument position based on the instrument position at times Ti near Tt, wherein the determination of a tissue parameter at a tip of the instrument is performed with a first calculation accuracy in a first mode of operation, and the determination of a tissue parameter at a tip of the instrument is performed with a second calculation accuracy in a second mode of operation, the second calculation accuracy being higher that the first calculation accuracy, and displaying on a display unit an image being a combination of a current image of the interior of a body and a representation of tissue parameter at the tip of the instrument at time Tt.

By recording a series or sequence of images of the interior of a body these images may be displayed to a user, so that the user may visually inspect the position of an instrument in the interior of the body. This allows the user to identify the position of the instrument in the body. The method determines the position of the instrument in the body in each image. These images are recoded at times Ti. The interval between the images may be constant or have variations. The user is usually most interested in having the most recent image displayed. Using the method a tissue parameter is determined. This determination may take longer than the interval between images. Thereby the tissue information may not be available when displaying the latest image, the method then displays the most recent available tissue information in the appropriate position. The method includes determining the tissue parameter with certain accuracy, depending on the mode of operation. In the first mode the tissue parameter will be available in less time than in the second mode, albeit with less accuracy. This less accuracy may be acceptable in certain circumstances.

The method according to the second aspect is advantageous in operating a system as defined in the first aspect. The method provides a way of ensuring that determination of tissue-type parameters is performed at an appropriate level so as to reduce calculation times in periods where the instrument is moved relatively fast.

The method may include using the first calculation accuracy the algorithm for determination of tissue parameter includes a first number of iterations and when using the second calculation accuracy the algorithm for determination of tissue parameter includes a second number of iterations, wherein the first number of iterations is lower than the second number of iterations.

In an embodiment the determination of the set of parameters indicative of tissue type comprises performing multivariate statistical analysis, such as PCA or partial least squares discriminant analysis.

A third aspect of the present invention relates to an instrument for use in a system for guiding the instrument in a body, the instrument comprising an optical probe, the system for guiding the instrument comprising: a medical imaging device configured for forming an image of the interior of the body, a tissue-type determination device configured to receive a tissue signal from an instrument, the tissue-type determination device configured to determine a set of parameters indicative of tissue type based on the tissue signal from the instrument, the tissue-type determination device being operable in two modes, a first mode where tissue-type determination is performed using a first accuracy and a second mode where tissue-type determination is performed using a second accuracy being higher than the first accuracy, the guidance system being configured for determining position of the instrument and storing a sequence of positions, the guidance system being configured for establishing a display image combining the image of the interior of the body and the set of parameters indicative of tissue type displayed at the recorded positions of the instrument, and a display device configured for displaying the display image. The instrument is advantageous in that it provides the user with a device that is detectable and viewable on a screen while providing a signal for tissue type determination to an associated system providing a user with information on both instrument position and tissue parameters important to the user.

The method according to the second aspect may be implemented in software (sometimes referred to as a computer program) and used in controlling a system according to the first aspect. The computer program, when executed by a digital processor, causes the processor to perform a method comprising displaying an image comprising tissue-type and instrument position in a body, the software implemented method comprising the steps of: recording a sequence of images of the interior of the body each at time Ti, determining an instrument position in each image of the interior of the body, determining at a tissue parameter at a tip of the instrument at time Tt and an estimated instrument position based on the instrument position at times Ti near Tt, wherein the determination of a tissue parameter at a tip of the instrument is performed with a first calculation accuracy in a first mode of operation, and the determination of a tissue parameter at a tip of the instrument is performed with a second calculation accuracy in a second mode of operation, the second calculation accuracy being higher that the first calculation accuracy, displaying on a display unit an image being a combination of a current image of the interior of a body and a representation of tissue parameter at the tip of the instrument at time Tt. The computer program is stored on a tangible non-transitory computer readable storage medium such as a compact disc read-only memory (CDROM), a digital versatile disc (DVD), a memory stick, a hard drive, or be accessible for download from a server or the like.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which FIG. 1 schematically illustrates a system according to the present invention, FIGS. 2 and 3 schematically illustrates states where an instrument is approaching a tissue border.

DESCRIPTION OF EMBODIMENTS

Figure 1:
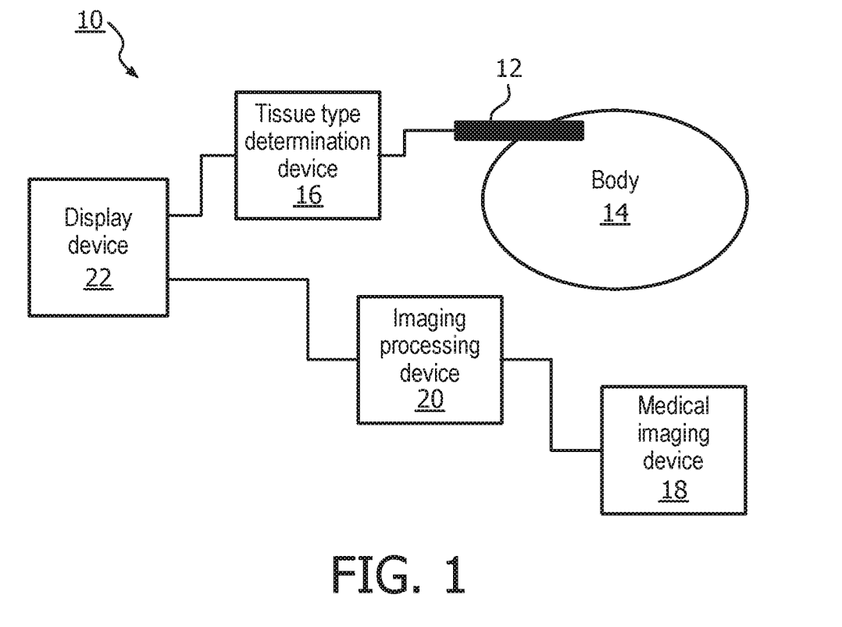

An embodiment of the invention is illustrated in FIG. 1 illustrating a guidance system 10 for guiding an instrument 12 in a body 14. The guidance system 10 comprises a medical imaging device 18 configured for forming an image of the interior of the body 14. The guidance system 10 comprises a tissue-type determination device 16 configured to receive a tissue signal from an instrument 12. The tissue-type determination device 16 is configured to determine a set of parameters indicative of tissue type based on the tissue signal from the instrument 12. The tissue-type determination device 16 is operable in two modes, a first mode where tissue-type determination is performed using a first accuracy and a second mode where tissue-type determination is performed using a second accuracy being higher that the first accuracy. The guidance system 10 is configured for determining position of the instrument 12 and storing a sequence of positions. The guidance system 10 is configured for establishing a display image combining the image of the interior of the body 14 and the set of parameters indicative of tissue type displayed at the recorded positions of the instrument. The guidance system 10 comprises a display device 22 configured for displaying the display image. The guidance system 10 comprises an image processing device 20 adapted or configured to perform the image processing steps.

The system records the data from the different sensors and detectors. This data is then used for two purposes, the real-time display to the user and for later analysis. For the real-time display there is a need for displaying the processed data as quick as possible. When the instrument 12 is not being moved fast, there is more time for processing the data and consequently a higher accuracy may be achieved. This is possible as the person using the instrument 12 is moving the instrument slowly or holding the instrument as still as possible.

The instrument 12 may be hand-held or supported by a guiding system or part of or attached to a robot arm or the like.

The instrument 12 comprises optical components to deliver an optical signal to the tissue and receive the return signal. The return signal is transmitted to the tissue-type determination device 16.

The present invention proposes that an optical console is used as the tissue-type determination device, which controls the instrument 12 and processes the received measurements. The optical console operates in at least two different modes: (1) a fast but less accurate mode providing fast processing of spectral analysis of the optical signal with reduced accuracy and (2) a slow but accurate mode of processing. When the instrument is advanced, the first mode of operation is employed in the optical console and during the more stationary phase where the instrument is substantially at the same location, the second mode is employed in the optical console.

The mode of operation may be determined from the movement of the instrument 12 detected in the image of the imaging device 20/18. If the speed of the movement is above a certain threshold then the first mode of operation is selected, otherwise the second mode is selected. Alternatively, the optical console is operated in the first mode (fast mode) unless a signal is presented to switch to the second mode. This may be a signal provided by the user. Different users may have different preferences as to the level of autonomy.

The imaging device is preferably an X-ray device capable of recording images of the interior of the body 14. The needle tracking device can be for instance as described in: Racadio, J. M., D. Babic, et al. (2007). "Live 3D Guidance in the Interventional Radiology Suite" Am. J. Roentgenol. 189 (6): W357-364. The optical console and interventional probe are for example as is described in R. Nachabé et al., "Estimation of biological chromophores using diffuse optical spectroscopy: benefit of extending the UV-VIS wavelength range to include 1000 to 1600 nm", Biomedical Optics Express 18 (2010) p1432.

In the following two different ways of determining tissue parameters is discussed. The methods may be used separately or in combination. Other method for optical investigation of the tissue may also be used in connection with the present invention.

Figure 5:
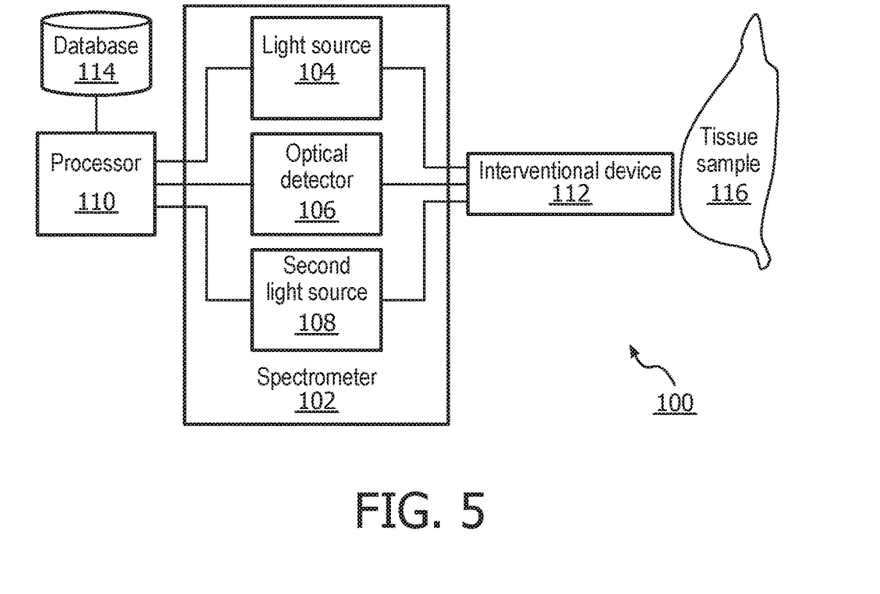
FIGS. 5 and 6 are schematic illustrations of system for optical investigation of tissue.

FIG. 5 shows a schematic view of an apparatus comprising a spectrometer 102 comprising a light source 104, an optical detector 106 and an interventional device 112, where the interventional device 112 has one or more guides, such as optical elements, such as optical waveguides, capable of guiding light from the light source 104 to a distal end of the interventional device so as to emit the light at the distal end of the interventional device, and furthermore capable of guiding light back from the distal end of the interventional device to the optical detector 106. The light guides enable light to enter an associated tissue sample 116 and the light guides further enable light exiting the associated tissue sample to be collected and led to the optical detector. The apparatus thus enables procurement of measured data representative of an optical spectrum of the associated tissue sample 116. The optical detector 106 may be controlled by processor 110 so as to acquire the measured data. The processor may have access to a database 114. In a specific embodiment, the apparatus is further arranged to access the database 114, where the database comprises predetermined data representative of an optical spectrum, such as an optical spectrum of a biomolecule, such as collagen and/or elastin, such as a plurality of optical spectra of different chromophores. This may enable the processor to better determine any one of the first parameter, the distortion parameter and the second parameter.

In the specific embodiment shown there is also a second light source 108. In this embodiment the first light source 104 is a lamp suited for Diffuse Reflectance Spectroscopy (DRS) and the second light source 108 is a LASER suited for fluorescence spectroscopy. In an alternative embodiment, there may be only a single light source, such as a single lamp which may then be used in combination with a switchable filter serving to limit the range of frequencies emitted and thereby narrowing the bandwidth and thereby obtaining an appropriate bandwidth for doing fluorescence spectroscopy.

Figure 6:
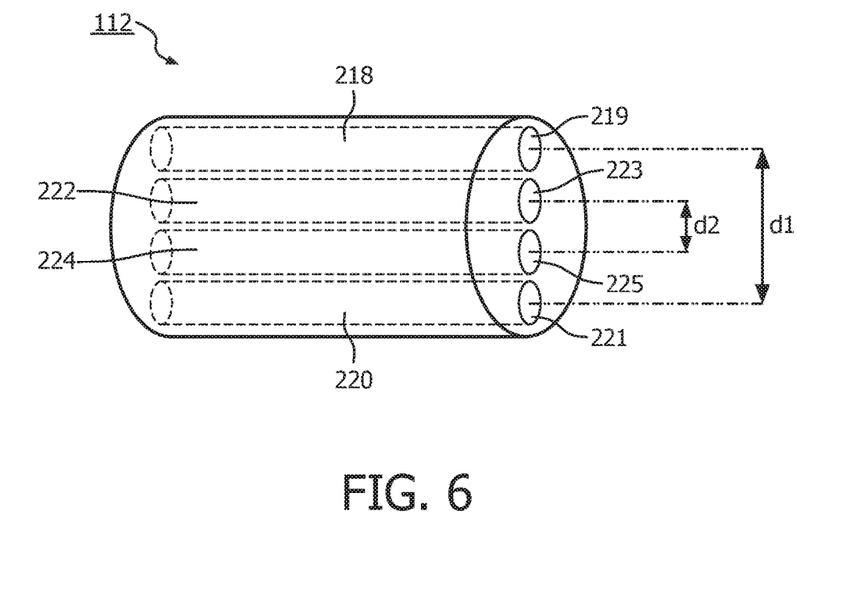

FIG. 6 shows a perspective illustration of an embodiment of an interventional device 112, which interventional device comprises a first guide 219, a second guide 221, a third guide 223 and a fourth guide 225. The figure shows an exit position 219 on distal end of the first guide and an entry position 221 on a distal end of the second guide. Similarly, there is shown an exit position 223 on distal end of the third guide and an entry position 225 on a distal end of the fourth guide. The drawing is not to scale. The first, second, third and fourth guide are understood to be light guides, such as optical fibres, such as optical waveguides. Furthermore is indicated the distance d1 between an exit position 219 on the first guide 218 and an entry position 221 on the second guide 220. Still further is shown a distance d2 between an exit position 223 on the third guide 222 and an entry position 225 on the fourth guide 224. Note that in a particular embodiment the interventional device may be constructed so as to optimise d1 for Diffuse Reflectance Spectroscopy. In another particular embodiment the interventional device may be constructed so as to optimize 2 for fluorescence spectroscopy.

In a specific embodiment there is provide an optical probe, such as the interventional device 112, is a needle with optical fibers 218, 220, 222, 224 that can be connected to an optical console, such as the spectrometer 102. The optical console contains a light source 104 enabling light to be provided via one of the fibers to the distal end of the optical probe. The scattered light is collected by another fiber and is guided towards the detector 106. The optical console may also contain a LASER source 108 with a wavelength lower than 450 nm in order to induce autofluorescence in the tissue sample. The obtained data, such as the first and/or second set of measured data are processed by processor 110 using a dedicated algorithm. For instance light is coupled out of the distal tip through at least one fiber, which serves as a source, and the wavelength is swept from e.g. 500-1600 nm or a broadband light source is used. The corresponding wavelength-dependent reflection is measured by at least one other fiber, which is spatially separated from the source, such as a distance d1 of at least 0.5, such as at least 1, such as at least 2 mm apart, such as at least 5 mm apart. The amount of reflected light measured at the "detection" fiber, is determined by the absorption and scattering properties of the probed structure (e.g. tissue sample). From this signal we can deduce the concentration of the chromophores such as blood, water, fat, collagen, bile, beta-carotene but also oxygenation of blood and scattering parameters. The autofluorescence is measured through a fiber that is in close vicinity with the excitation fiber, such as within a distance d2 being less than 5 mm, such as less than 2 mm, such as less than 1 mm, such as less than 0.5 mm, such as less than 0.25 mm. The measured autofluorescence is corrected for scattering and absorption such that the estimated intrinsic fluorescence is obtained. From this the concentration of fluorophores such as NADH, FAD, collagen and elastin can be measured.

In a specific embodiment, the apparatus comprises a light source 104 in the form of a halogen broadband light source with an embedded shutter, an interventional device 112 with four guides and an optical detector 106 that can resolve light across a span of wavelengths, such as substantially in the visible and infrared regions of the wavelength spectrum, such as from 400 nm to 1700 nm. The apparatus may furthermore comprise a filter that rejects light for wavelengths below 465 nm which filter may be mounted in front of the optical detector 106 to reject second order light at the optical detectors during diffuse reflectance spectroscopy. The interventional device 112 has a first guide connected to the light source, the second guide connected to the optical detector 106. The centre-to-centre distance separation d1 between the exit position 219 on the first (emitting) guide 218 and the exit position 221 on the second (collecting) guide 220 may be in the millimeter range, such as at least 1 mm, such as at least 2 mm, such as 2.48 mm. All guides may be low-OH fibres of core diameters in the micron range, such as core diameter of 200 microns. Fibres containing low-OH, sometimes also called VIS-NIR fibres, are typically suitable for the visible (VIS) and near infrared (NIR) part of the optical spectrum.

In an alternative embodiment a plurality of optical detectors are applied, such as two optical detectors that can resolve light in different length regions, such as substantially in the visible and infrared regions of the wavelength spectrum respectively, such as from 400 nm to 1100 nm and from 800 nm to 1700 nm respectively.

In a particular embodiment diffuse reflectance spectroscopy is used for obtaining the first set of measured data representative of an optical spectrum and fluorescence spectroscopy is used for obtaining the second set of measured data representative of an optical spectrum. Other optical methods can be envisioned, such as fluorescence spectroscopy measurements, diffuse optical tomography by employing a plurality of optical fibres, differential path length spectroscopy, or Raman spectroscopy.

Preferably, the optical console allows for the fluorescence excitation wavelength to be changed. This could be accomplished with multiple sources that are switched or multiplexed (e.g. frequency modulated) or with a tunable source. Measuring different fluorescence emission spectra at different excitation wavelengths would provide information that is potentially relevant for differentiating collagen and elastin (and additionally different types of collagen).

Two-photon fluorescence excitation could also be utilized. This may have the benefits of deeper penetration depth relative to one-photon excitation. The volumes probed with two-photon fluorescence measurements may be more similar to the volumes probed for diffuse reflectance measurements in the infrared.

To perform an optical analysis of the tissue in front of the instrument three steps have to be performed. In the first step the spectroscopic measurement is performed. Light, i.e. an optical signal, is send to the distal end of the instrument where it interacts with the tissue and the light reaching the light guide of the instrument again is guided to a spectrometer. The spectrometer transforms the signal into a spectrum. All these elements account for approximately 0.2 s amount of time in a fast way of measuring and in 1 s up to 2 s for an accurate high signal-to-noise level. In the second step the measured spectra is translated into tissue parameters. This step can, depending on the accuracy of the fit, range from 0.2 s in fast mode to 1 s up to 3 s in accurate mode. In the third step the optical information is send to the imaging device 20 in which the data is linked to the location of the instrument tip and displayed in the image.

Instead of extracting physiological parameters we can do also feature extraction in the first mode. This means that the spectra are not fitted by a physical model but the algorithm is based on changes in the spectra at a certain wavelength or several discrete wavelength bands.

Figure 2:
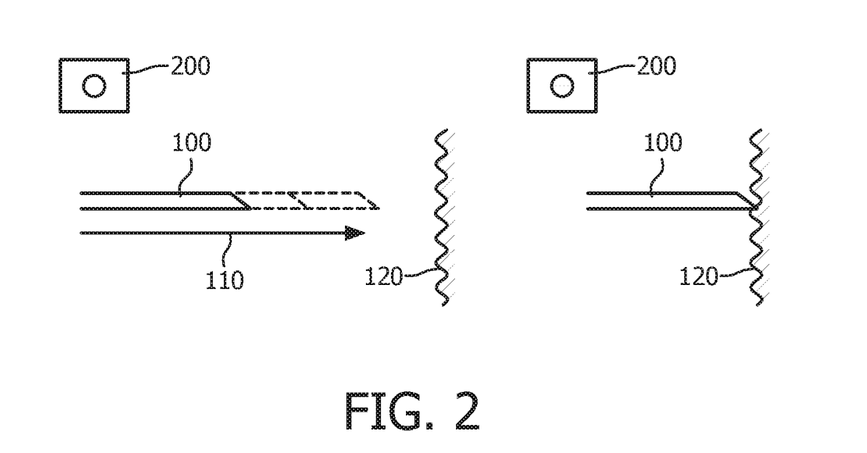

In a preferred embodiment, the optical analysis in 'fast mode' is optimized for fine guidance during fast advancement of the instrument, providing feedback on major changes of selected tissue parameters, giving the operator a basis for decision-making of when to switch to stationary measurements in 'accurate mode', see FIG. 2. For instance, during the fast advancement (110) of the instrument (100), the optical spectra obtained in fast mode can be translated into a simple binary signal (200), such as: tissue boundary reached, Yes/No, allowing for fine guidance the instrument to tissue boundaries (120) not visible under X-ray image guidance. This may include boundaries of tumor/normal tissue, or ablated/non-ablated tissue, or the wall of blood vessels.

Once a tissue boundary is reached, the feedback to the operator can comprise an acoustical and/or optical signal (200), whereby the latter may be linked to the image display 22.

In another embodiment, different operation modes of the optical console, i.e. the tissue-type determination device, can be used when the instrument is positioned in a stationary location, thereby monitoring small displacements of the instrument tip from the target location due to movements in the body. For instance, during percutaneous interventions in the vicinity of the lung or the heart, see FIG. 3, tissue movements (310) due to breathing or heart beating can displace the instrument (100A) from the target (300), in particular when the target is small, such as a lesion of only a few millimeter in size.

Figure 3:
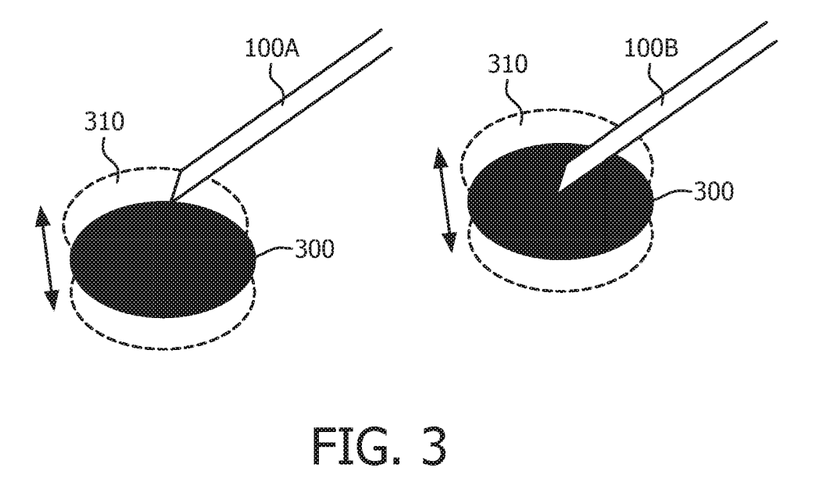

The operation mode of the tissue-type determination device ('fast' or 'accurate' or additional modes) can be chosen accordingly to ensure an optimal balance between the desired accuracy of tissue discrimination and the speed of movements at the target. For instance the signal obtained from the optical analysis allows for verifying the position of the instrument (100A) at the target based on tissue information. This enables the physician to fine-adjust the position if required (100B). The possibility for fine-adjusting the instrument position with fast optical feedback can be particularly useful for taking biopsies at locations which are subject to movements in the body.

One way to realize high and low accuracy modes is to use very short measurement times, but then do a weighted average of the last x measurements. The weighting would ensure that the most recent measurements (which have been performed closest to the current instrument tip location) carry a higher weight than measurements done further along the trajectory. Using this method you automatically get higher accuracy, if you move the instrument more slowly, plus you get a near continuous line of measurements. The high accuracy button, can then improve the result by averaging over more measurements. The averaging can also be adopted automatically. For example in tissues with a low blood content, the signal-to-noise ratio is very high, so it is not needed to average over as many measurements as would be needed in a blood rich tissue.

To decide on switching between the "lower accuracy mode" and "high accuracy mode", we can use the following methods:

Information from imaging modality (for instance from tracking the instrument in the image we can determine the insertion speed and when this is below a certain values we use the second mode etc.)
A decision of the physician
Information from the spectra In addition this decision could be based on other parameters, e.g. info from another measurement modality, such as Electromagnetic tracking, optical shape sensing based for instance on Fiber Bragg Gratings. A FBG is a segment of a longer optical fiber that reflects light in a particular relatively narrow range of wavelengths and transmits light in other ranges. The reflection of light in a particular narrow wavelength range is achieved by adding periodic variations to the refractive index of the fiber core at specific intervals, which creates a wavelength-specific dielectric mirror. In another embodiment of an FBG the variations may run along the entire length of the fiber. The iU22 xMATRIX Ultrasound System with PercuNav is an example of a system utilizing electromagnetic tracking.

Further a small camera through which the fiber is guided during instrument insertion could be provided. The camera could detect instrument movement via movement of the fiber, we could also add small stripes on the fiber for easier movement detection.

Another embodiment is where the instrument is equipped with an accelerometer. Depending on a pre-determined threshold for acceleration the system switch from one mode to the other.

Further the guidance system could comprise an instrument speed analyzer for determining present speed of the instrument, if the present speed of the instrument is above a speed threshold the tissue-type determination device being operated in the first mode, if the present speed of the instrument is below a speed threshold the tissue-type determination device being operated in the second mode. This could be an image processing device extracting the instrument speed from two or more images. Regarding speed threshold, presently a resolution of 1 to 2 mm is required in position. In the slow mode, or high accuracy mode, the measurement time and analysis takes about 1 sec. The threshold could then be selected as <1 mm/s for which the accurate mode can be used. The threshold could be in the range 0.5 mm/second to 100 mm/second depending on the requirements set by the user. It is most likely that the presently preferred threshold will be in the range 1 mm/second to 20 mm/second. The threshold may be set by the user via an input device of the system thereby allowing the person using the system to control the operation of the system to a higher degree in accordance with personal preferences.

Also take into account that in the future the speed of the computer increases and the detectors become more sensitive so that so that the slow speed may decrease from is now to 0.5 s in future.

Figure 4:
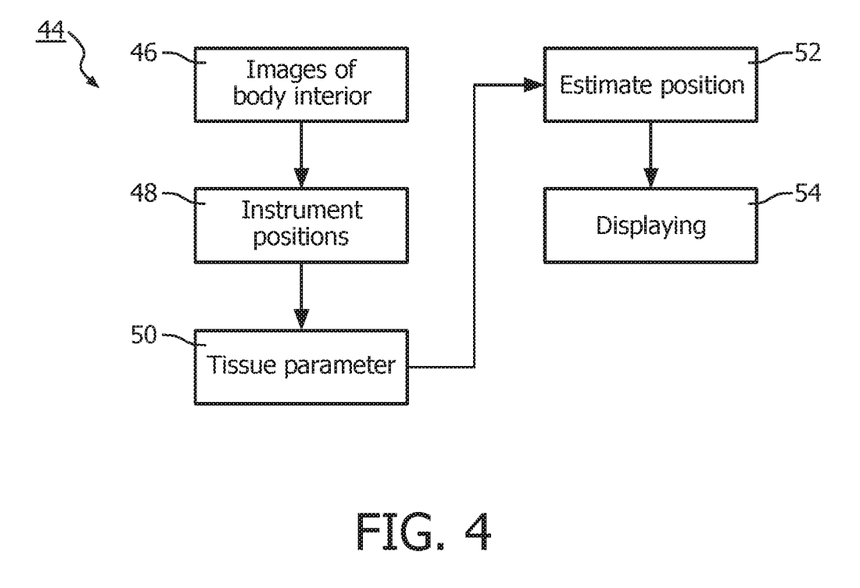
FIG. 4 is a schematic illustration of steps in a method according to the present invention.

FIG. 4 schematically illustrates steps of a method 44 of displaying an image comprising tissue-type and instrument position in a body. The method 44 comprises the step of recording a sequence of images of the interior of the body each at time Ti. The method 44 comprises the step of determining an instrument position in each image of the interior of the body. The method 44 comprises the step of determining at a tissue parameter at a tip of the instrument at time Tt and an estimated instrument position based on the instrument position at times Ti near Tt. The method 44 comprises the step of wherein the determination of a tissue parameter at a tip of the instrument is performed with a first calculation accuracy in a first mode of operation, and the determination of a tissue parameter at a tip of the instrument is performed with a second calculation accuracy in a second mode of operation, the second calculation accuracy being higher that the first calculation accuracy. The method 44 comprises the step of displaying on a display unit an image being a combination of a current image of the interior of a body and a representation of tissue parameter at the tip of the instrument at time Tt.

As mentioned the adaptation of the calculation accuracy allow for updating the tissue parameters during movement provides the best possible information to the user at any given time.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A guidance system for guiding an instrument in a body, the guidance system comprising:
    a medical imaging device configured for forming an image of an interior of the body;
    a tissue-type determination device configured to receive a tissue signal from an instrument the tissue-type determination device configured to determine a set of parameters indicative of tissue type based on the tissue signal from the instrument, the tissue-type determination device configured to operate in a first mode, wherein tissue-type determination requires a first calculation time, and in a second mode, wherein tissue-type determination requires a second calculation time that is longer than the first calculation time, wherein the first mode is faster than the second mode;
    the guidance system being configured for determining a position of the instrument and storing a sequence of positions;
    the guidance system being configured for establishing a display image combining the image of the interior of the body and the set of parameters indicative of tissue type displayed at recorded positions of the instrument; and
    a display device configured for displaying the display image.

2. The guidance system according to claim 1, further comprising:
    an instrument speed analyzer for determining present speed of the instrument, wherein when the present speed of the instrument is greater than a speed threshold, the tissue-type determination device being operated in the first mode, and when the present speed of the instrument is less than a speed threshold the tissue-type determination device being operated in the second mode.

3. The guidance system according to claim 2, wherein the speed threshold is in a range 0.5 mm/second to 20 mm/second.

4. The guidance system according to claim 1, further comprising:
    an input device for supplying a tissue-type determination mode signal to the tissue-type determination device instructing the tissue-type determination device to operate in the first mode or the second mode.

5. The guidance system according to claim 1, wherein the medical imaging device comprises an x-ray device.

6. The guidance system according to claim 1, wherein the tissue-type determination device is an optical console which obtains an optical spectrum, and processes the optical spectrum to determine the set of parameters indicative of tissue type.

7. The guidance system according to claim 1, further comprising a mode indicator for communicating to a user when the tissue-type determination device operates in the first mode or the second mode.

8. The guidance system according to claim 1, wherein the guidance system comprises a processor arranged for receiving signals relating to the set of parameters indicative of tissue type and the sequence of positions of the instrument, and the processor is arranged for establishing the display image.

9. The guidance system according to claim 1, wherein the tissue-type determination device is an optical console and wherein the guidance system is arranged so as to obtain a diffuse reflectance spectroscopy spectrum and/or fluorescence spectroscopy spectrum and/or Raman spectroscopy spectrum from the optical console.

10. The guidance system according to claim 1, wherein the determination of to the set of parameters indicative of tissue type comprises:
    performing multivariate statistical analysis, such as PCA or partial least squares discriminant analysis.

11. A method of displaying an image comprising tissue-type and instrument position in a body, the method comprising:
    receiving a sequence of images of an interior of the body each at a time Ti;
    determining an instrument position in each image of the interior of the body;
    determining at a tissue parameter at a tip of the instrument at time Tt and an estimated instrument position based on the instrument position at times Ti near a time Tt, wherein the determining of the tissue parameter at a tip of the instrument is performed with a first calculation time in a first mode of operation, or the determination of a tissue parameter at a tip of the instrument is performed with a second calculation accuracy in a second mode of operation, a second calculation time being higher than the first calculation time, wherein the first mode is faster than the second mode; and
    displaying on a display unit an image comprising a combination of a current image of the interior of a body and a representation of tissue parameter at the tip of the instrument at time Tt.

12. The method according to claim 11, wherein using the first mode for determining the tissue parameter requires a first number of iterations and using the second mode for determining the tissue parameter requires a second number of iterations, wherein the first number of iterations is lower than the second number of iterations.

13. The method according to claim 11, wherein the determination of to the set of parameters indicative of tissue type comprises:
    performing multivariate statistical analysis, such as PCA or partial least squares discriminant analysis.

14. A non-transitory computer-readable medium embodied with a computer program comprising computer code for execution by a processor, the computer code comprising:
    a first code portion for receiving a sequence of images of an interior of a body each at a time Ti;
    a second code portion for determining an instrument position in each image of the interior of the body;
    a third code portion for determining at a tissue parameter at a tip of the instrument at time Tt and an estimated instrument position based on the instrument position at times Ti near a time Tt, wherein the determining of the tissue parameter at a tip of the instrument is performed with a first calculation time in a first mode of operation, or the determination of a tissue parameter at a tip of the instrument is performed with a second calculation accuracy in a second mode of operation, a second calculation time being higher than the first calculation time, wherein the first mode is faster than the second mode; and a fourth code portion for displaying on a display unit an image comprising a combination of a current image of the interior of a body and a representation of tissue parameter at the tip of the instrument at time Tt.

* * * * *